United States Patent [19]

Kuo et al.

[11] 4,163,698

[45] Aug. 7, 1979

[54] IN SITU REFERENCE ELECTRODE FOR DIAPHRAGM CELLS

[75] Inventors: Han C. Kuo, Cleveland; George W. Geren, Georgetown; Thomas E. Corvin; Byung K. Ahn, both of Cleveland, all of Tenn.

[73] Assignee: Olin Corporation, New Haven, Conn.

[21] Appl. No.: 908,434

[22] Filed: May 22, 1978

[51] Int. Cl.² ............................................. G01N 27/30
[52] U.S. Cl. ........................................ 204/1 T; 204/98; 204/195 F; 204/256; 204/258
[58] Field of Search ............ 204/98, 256, 258, 195 F, 204/1 T

[56] References Cited

U.S. PATENT DOCUMENTS 3,291,714  12/1966  Hall et al. ............................ 204/256
3,632,498  1/1972   Beer .................................... 204/290 F

FOREIGN PATENT DOCUMENTS 1304849  1/1973  United Kingdom ................ 204/195 F

OTHER PUBLICATIONS

Reprint from Corrsion, vol. 16, No. 2, Feb. 1960, pp. 47t to 54t.

Primary Examiner—T. Tung
Attorney, Agent, or Firm—Bruce E. Burdick; Donald F. Clements; Thomas P. O'Day

[57] ABSTRACT

A method and apparatus for measuring the overvoltage of a gas producing electrode of a chlor-alkali diaphragm cell is disclosed. The method includes positioning an exposed metal tip of a reference electrode from about 0.2 to about 1.0 mm away from the gas producing electrode within a stream of gas produced by the gas producing electrode. The apparatus includes the reference electrode so positioned. Platinized platinum wire and a $RuO_2$—$TiO_2$ coated Ti wire are preferred as the reference electrodes for cathode and anode, respectively.

17 Claims, 4 Drawing Figures

IN SITU REFERENCE ELECTRODE FOR DIAPHRAGM CELLS

This invention relates generally to electrolytic cells, and particularly to apparatus for measuring overvoltage of electrodes of such cells.

"In-situ" as used herein means physically positioned in the environment and at the location where the property to be measured exists. In the case of electrode overvoltage of a gas-producing electrode, this means adjacent that electrode and within the stream of gas produced by said electrode. "Diaphragm cell" means a diaphragm or membrane type cell. "Tip" as used herein means a three-dimensional end portion as opposed to the two-dimensional very end surface area.

Conventionally, overvoltages of electrodes of diaphragm cells have been measured by use of a Luggin capillary tube passing from adjacent the electrode as seen in FIG. 2 through the cell housing to a reference electrode outside the electrolytic cell. As described in U.S. Pat. No. 3,291,714 issued Dec. 13, 1966 to J. R. Hall et al and shown in FIG. 1 of said Hall et al patent, such a Luggin capillary tube conventionally penetrates the cell wall at the top of the cell through a polyethylene washer and extends downwardly to a position slightly spaced from the center of the cathode. The Luggin capillary tube is connected by a salt bridge to an individual calomel reference electrode located outside the cell. Such a reference electrode is not "in-situ" as defined above. Also, these Luggin capillaries are conventionally not part of the cell assembly in the form in which it would be used in commercial operations but are included to permit overvoltage measurements to be made during laboratory testing. The conventional combination of a Luggin capillary tube and external reference electrode suffers from several problems. First, the impedance indication given by the Luggin capillary and salt bridge method conventionally used is so high that a very elaborate and hence expensive high impedance voltmeter is required to make the measurement. The capillary tube sometimes becomes blocked by gas generated from the electrode, especially where, as in the above-noted Hall et al patent, the tube passes upwardly and out through the top of the cell. Also, the electrolyte often must be drawn through the capillary tube with a syringe or other suction device in order to have sufficient flow, and there is difficulty in guaranteeing that the electrolyte to which the saturated calomel electrode (S.C.E.) is continuously connected is identical to the electrolyte to which the electrode being tested is actually exposed in-situ.

A solution to these and other problems is provided by the apparatus of the present invention which comprises an in-situ reference electrode assembly for measuring overvoltage of a gas producing electrode of a chlor-alkali diaphragm cell which includes a metal tip of reference electrode immersed in the same electrolyte as said gas producing electrode and positioned from about 0.2 to about 1.0 millimeters away from said gas producing electrode within the stream of gas produced by said gas producing electrode during electrolysis.

The invention also provides a method for measuring the overvoltage of a gas producing electrode of a chlor-alkali diaphragm cell, which comprises the step of positioning a reference electrode immersed in the same electrolyte as said gas producing electrode, and at a location of from about 0.2 to 1.0 millimeters away from said gas producing electrode within the stream of gas produced by said gas producing electrode.

The invention will be better understood by reference to the attached drawings, which show a preferred embodiment of the invention by way of example and in which.

Figure 1:
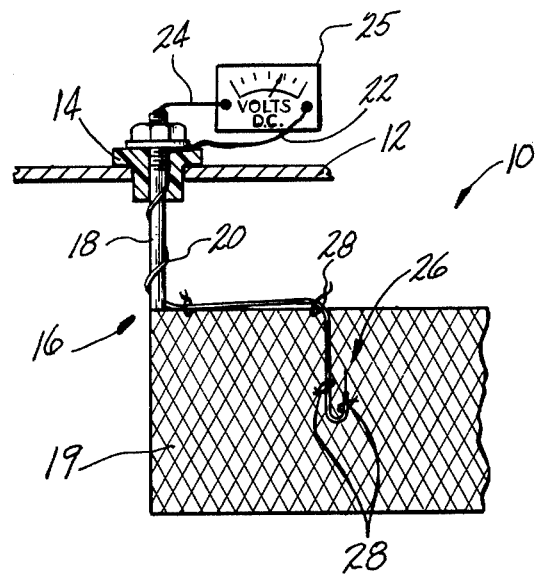
FIG. 1 is a schematic, vertical, cross-sectional view through a diaphragm cell, parallel to the electrodes, so as to show a side elevational view of a working electrode with the reference electrode of the invention attached thereto.

FIG. 1 shows the attachment of the in-situ reference electrode to a working electrode of a cell 10. Cell 10 can be of any conventional design which includes an electrode support wall or top 12, a cell top seal 14 and an electrode 16. Electrode 16 has a stem 18 which passes through seal 14 and cell top 12 to the exterior of cell 10. Electrode 16 also has a working face 19 supported by and conductively attached to stem 18. For purposes described below, an insulating tube 20 with a wire 22 therein also passes through seal 14. The invention could also be utilized with conventional bottom or side supported electrodes substituted for top supported electrode 16, which is merely the preferred electrode with which the invention can be used. Stem 18 is connected to an external source (not shown) of positive or negative direct current in conventional manner to electrolyze an electrolyte and produce, as a product or by-product, a gas. The production of such gas results in a measurable polarization or overvoltage of the gas producing electrode.

For example, electrode 16 could be the cathode or anode of a diaphragm type electrolytic cell for the electrolysis of concentrated brine to produce chlorine gas and caustic soda, with hydrogen gas and overflow brine and byproducts. In the case of such a cell, chlorine gas is conventionally produced at the anode and a chlorine overvoltage would exist at the anode. In the case of such a cell, hydrogen gas is conventionally produced at the cathode and a hydrogen overvoltage would exist at the cathode. These overvoltages are directly measured by an in-situ reference electrode assembly 26 and method of measurement, which are the subject of this invention.

Figure 4:
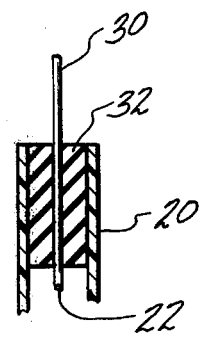
FIG. 4 is a cross-section through the tip of the reference electrode of FIGS. 1 and 3.
Figure 3:
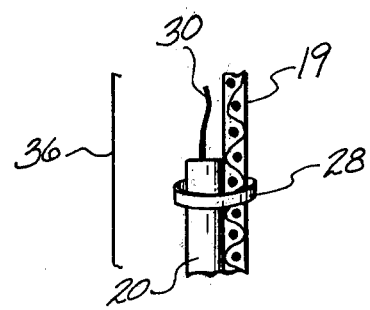
FIG. 3 is a schematic, vertical cross-section through the center of the diaphragm cell of FIG. 1 showing the reference electrode of the invention.

Reference electrode assembly 26 as shown in FIGS. 1, 3 and 4, comprises insulating tube 20, reference wire 22, stem wire 24, fasteners 28, tip seal 32 and a voltmeter 25. Insulating tubing 20 is a chemically-resistant, non-conductive tubing such as polyethylene, polypropylene or tetrafluoroethylene which serves to insulate reference wire 22 from electrode 16. Reference wire 22 is a small gauge, preferably 20–22 gauge, wire of a material suitable for use as a reference electrode. Where electrode 16 is a cathode, wire 22 is preferably platinum. Where electrode 16 is an anode, wire 22 is preferably a small gauge, preferably 20–24 gauge, titanium wire coated with a ruthenium oxide-titanium oxide alloy or mixed crystal.

The in-situ reference electrode 26 of the invention can be assembled by placing a small gauge, such as for example a 20-24 gauge, wire of material suitable as a reference electrode in a chemically-resistant tubing, leaving tip 30, approximately 0.3 to 0.7 cm of the wire, exposed. A platinized platinum wire has been found to be particularly suitable as the small gauge wire in an in-situ reference electrode for measuring hydrogen overvoltage of a hydrogen producing cathode of an electrochemical cell. A small gauge (e.g. 20-24) conductive wire comprised of a valve metal selected from the group consisting of tantalum, titanium, zirconium, bismuth, tungsten, niobium and alloys thereof, such as for example a titanium wire, coated with a mixed-crystal material consisting essentially of at least one oxide of a film-forming metal and at least one oxide of a platinum group metal, such as for example a titanium dioxide ($TiO_2$) and ruthenium dioxide ($RuO_2$) coating, according to U.S. Pat. No. 3,632,498, issued Jan. 4, 1972 to H. B. Beer, is suitable as the small gauge wire in an in-situ reference electrode for measuring chlorine overvoltage of an anode in a chlorine gas producing electrolytic cell.

A suitable ruthenium oxide-titanium oxide coated titanium wire can be produced by the following process. A small gauge titanium wire is etched in an aqueous solution of about 35-38 weight percent HCl, about 0.25-1.0 weight percent HF and about 61-64 weight percent water for about 50-90 seconds and then etched in 36 percent HCl for 2-3 hours at room temperature. After this etching, the wire is soaked in deionized water for about 12-20 hours. The wire is then removed from the deionized water and etched again in 36 percent HCl, this time for about 5-10 minutes to produce a "clean" titanium wire. Similar cleaning pretreatments would be used on the other alternate metals above-noted to remove any coatings or films. After this etching, a ruthenium chloride plating solution is brushed on the clean titanium wire. One suitable ruthenium chloride plating solution is a mixture of 6.2 ml butanol, 0.4 ml of 36 percent HCl, 6 ml of tetra-n-butyl-orthotitanate and 2 grams ruthenium chloride such as disclosed in Example II of U.S. Pat. No. 3,632,498 issued Jan. 4, 1972 to H. B. Beer. The wire is then heated in air at 300°-500° C. for 1-6 minutes. The brushing and firing procedure is repeated several times, such as for example four times and then the wire is heated in air at 300°-500° C. for 4-8 hours and air cooled to ambient temperature. The various other mixed crystal coatings could also be utilized following routine testing to determine if corrosion resistance and stability of overvoltage was equivalent to the $TiO_2$—$RuO_2$ coating described above.

Wire 22, whether for use as a cathode or anode reference electrode, is placed in the chemically resistant insulating tubing 20 with about a 0.3-1.0 cm tip 30 of wire 22 exposed, such as for example seen in FIGS. 3 and 5. The tip 30 is then sealed with a chemically resistant material, such as for example a silicon rubber or epoxy. This insulated wire is then attached to face 19 of electrode 16 adjacent the center of face 19 or at any other desired position. It is preferred to place the exposed tip 30 parallel to and from a lower limit of about 0.2 to an upper limit of about 1.0 millimeters away from the surface of electrode 19. The lower limit is set so as to avoid shorting between electrode 19 and tip 30 and to prevent bubbles being trapped between electrode 19 and tip 30. The upper limit prevents tip 30 from being outside the gas stream generated by electrode 19. It is preferred that tip 30 be pointed upwardly so that gas bubbles have less tendency to collect on tip 30 than would be the case if the tip were pointed down, since pointing tip 30 down would leave the seal 32 and end of tube 20 as downward facing ledges to hold or slow gas bubble release. Tube 20 can be attached to the cathode by any corrosion resistant fastening means such as for example a tetrafluoroethylene tie. Tube 20 can be either spaced from or in contact with the surface of electrode 16 since tube 20 is of insulating material. The end of wire 22 opposite tip 30 is also exposed so that a connection can be made to a first input terminal of a DC voltmeter 25 to measure the difference between the potential of wire 22 and electrode 16. Stem wire 24 serves to connect a second input terminal of DC voltmeter 25 to electrode 16 for purposes of making such a comparison. Voltmeter 25 can be any conventional readily available DC millivoltmeter and need not be an elaborate or sophisticated device as is conventionally needed in order to get a reliable overvoltage reading with a Luggin type measurement method. The overvoltage is read directly from a relatively inexpensive DC voltmeter 25 under normal operating conditions and is thus particularly suited for incorporation into production type diaphragm or membrane cells for which overvoltage has not previously been monitored on a regular basis, even though such information is quite valuable as an indication of the performance of the catalytic metal coatings normally used on electrodes of such cells.

Figure 2:
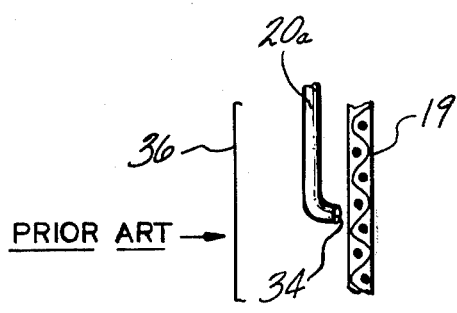
FIG. 2 is a schematic, vertical cross-section through the center of a prior art diaphragm cell at 90° to the electrodes showing a Luggin capillary.

FIG. 2 shows a conventional Luggin capillary tube 20a with an opening 34 adjacent an electrode 19 in a cell with a diaphragm or membrane 36. FIG. 3 shows a typical reference electrode tip 30 in an insulative tube 20 substituted for Luggin tube 20a. Membrane 36, which is also shown for reference in FIG. 3, can be of any conventional membrane material.

The invention is illustrated by, but not limited to the following examples.

EXAMPLE 1

A 20 gauge platinum wire was sealed in a polyethylene insulative tube leaving a 1.0 cm tip exposed. The end of the tube adjacent the tip was sealed with a silicon rubber glue and the exposed platinum wire is then platinized with black platinum. This electrode was then attached to a bench scale cell cathode as in FIGS. 1, 3 and 4 by a tetrafluoroethylene ring. A DC voltmeter was attached across the platinized wire and the cathode and the cathode overvoltage was read directly from the voltmeter under normal operating conditions. The readings were found to be in conformity with readings previously taken from a conventional Luggin capillary probe.

EXAMPLE 2

A 20 gauge titanium wire is coated with a titanium oxide ($TiO_2$)-ruthenium oxide ($RuO_2$) coating by using the following procedure:
1. The titanium wire was etched in a solution of 99 parts by volume concentrated (36%) HCl and one part by volume concentrated (50%) HF for one minute.
2. The wire was removed from the HCl—HF solution, etched in HCl (36%) for 2 and ½ hours at room temperature and then removed.
3. The wire was soaked in deionized water for 16 hours (i.e. overnight) until just before coating.
4. The wire was removed from the deionized water and etched for 8 minutes in concentrated (36%) HCl just before coating and then rinsed with deionized water.

5. A ruthenium chloride (RuCl$_3$) plating solution having, per gram of RuCl$_3$, 6.2 ml butanol, 0.4 ml concentrate (36%) HCl and 6 ml (5.46 grams) tetra-n-butyl-orthotitanate was brushed on the wire.
6. The solution covered wire was then heated in air ("fired") at 400° C. for 5 minutes.
7. Steps 5 and 6 above were repeated four times.
8. The coated wire was then heated in air at 400° C. for six hours and allowed to air cool to room temperature to give the coating greater stability.

The coated wire was then placed in a polyfluorinated hydrocarbon insulating tube leaving a tip of about one centimeter of coated wire exposed. The tube was sealed at this tip with a silicon rubber glue to prevent leakage.

This insulated coated wire was then attached as an in-situ reference electrode to an anode of a chlor-alkali electrolytic cell (see FIG. 1) in a position parallel the surface of said anode and with a fixed gap of 0.5 mm between the tip and the anode surface.

To monitor anode overvoltage, a DC voltmeter was attached across the coated titanium wire and the anode and the chlorine overvoltage of the anode was read directly from the voltmeter under normal operating conditions.

The readings were found to be in conformity with readings taken from a conventional Luggin capillary probe.

What is claimed is:

1. A method for directly measuring the overvoltage of a gas producing electrode of a chlor-alkali diaphragm cell during electrolysis and generation of gas, which comprises the step of positioning an exposed metal tip of a reference electrode, immersed in the same electrolyte as said gas producing electrode, at a location of from about 0.2 to about 1.0 mm away from said gas producing electrode within a stream of gas produced by said gas producing electrode during electrolysis and measuring the potential difference between said reference electrode and said gas producing electrode during electrolysis and generation of gas.

2. In an electrochemical chlor-alkali diaphragm cell having a gas producing electrode, the improved method of measuring the overvoltage of said electrode, which comprises the steps of:
   (a) positioning a small gauge reference electrode wire sealed in a chemically resistant insulating tube in such a position that said wire passes from the exterior of said cell to the interior of said cell with a 0.3–0.7 cm exposed tip of said wire outwardly projecting into said cell beyond a first end of said tubing;
   (b) attaching said tubing to said gas producing electrode with said exposed tip parallel to a surface of said electrode with a fixed gap of from 0.2 mm to 1.0 mm between said tip and said electrode; and
   (c) attaching a direct current voltmeter to said electrode and to said reference electrode wire to produce a direct reading of said overvoltage.

3. The method of claims 1 or 2 wherein said electrode is a cathode.

4. The method of claim 3 wherein said reference wire is a platinized platinum wire.

5. The method of claim 2 wherein said step of attaching said tubing includes a step of positioning said tubing so that said tip points up vertically when said electrode is in normal operating position.

6. The method of claims 1 or 2 wherein said electrode is an anode.

7. The method of claim 6 wherein said reference electrode comprises an electrically conductive base selected from the group consisting of tantalum, titanium, zirconium, bismuth, tungsten, niobium and alloys thereof, at least a portion of the surface of said base having a coating of a mixed crystal material consisting essentially of at least one oxide of a film-forming metal and one oxide of a platinum metal group.

8. The method of claim 7 wherein said conductive base is titanium and said coating is a mixture of ruthenium oxide and titanium oxide.

9. A in-situ reference electrode assembly for measuring overvoltage of a gas producing electrode of a chlor-alkali diaphragm cell, which comprises a metal tip of a reference electrode immersed in the same electrolyte as said gas producing electrode and positioned from about 0.2 to about 1.0 millimeters away from said gas producing electrode within the stream of gas produced by said gas producing electrode and voltmeter means, electrically connected to said gas producing electrode and said metal tip, for measuring differences in potential, if any, between said gas producing electrode and said metal tip.

10. The in-situ reference electrode assembly of claim 9 wherein said electrode comprises an exposed tip of an insulated wire, said tip being substantially parallel to a working face of said electrode.

11. The in-situ reference electrode of claim 10 further comprising fastening means, for supporting said exposed tip from said electrode, while insulating said tip from electrical contact with said gas producing electrode except through said electrolyte adjacent said gas producing electrode.

12. The electrode assembly of claims 9, 10 or 11 further comprising a voltmeter means, electrically connected to said in-situ reference electrode and said gas producing electrode for measuring the potential difference therebetween to produce a direct reading of overvoltage of said electrode.

13. The electrode assembly of claims 9 or 10 wherein said gas producing electrode is a cathode.

14. The electrode assembly of claim 13 wherein said in-situ reference electrode comprises platinized platinum.

15. The electrode assembly of claims 9 or 10 wherein said gas producing electrode is an anode.

16. The electrode assembly of claim 15 wherein said reference electrode comprises an electrically conductive base selected from the group consisting of tantalum, titanium, zirconium, bismuth, tungsten, niobium and alloys thereof, at least a portion of the surface of said base having a coating of a mixed crystal material consisting essentially of at least one oxide of a film-forming metal and one oxide of a platinum group metal.

17. The electrode assembly of claim 16, wherein said conductive base is titanium and said coating is a mixture of ruthenium oxide and titanium oxide.

* * * * *